(12) United States Patent
Lovald et al.

(10) Patent No.: US 8,246,663 B2
(45) Date of Patent: Aug. 21, 2012

(54) OSTEOSYNTHESIS PLATE, METHOD OF CUSTOMIZING SAME, AND METHOD FOR INSTALLING SAME

(75) Inventors: Scott Traver Lovald, Albuquerque, NM (US); Jon D Wagner, Albuquerque, NM (US)

(73) Assignee: Scott Lovald, San Francisco, CA (US)

( * ) Notice: Subject to any disclaimer, the term of this patent is extended or adjusted under 35 U.S.C. 154(b) by 1277 days.

(21) Appl. No.: 11/716,762

(22) Filed: Mar. 12, 2007

(65) Prior Publication Data

US 2007/0238069 A1 Oct. 11, 2007

Related U.S. Application Data

(60) Provisional application No. 60/790,488, filed on Apr. 10, 2006, provisional application No. 60/850,207, filed on Oct. 10, 2006.

(51) Int. Cl.
*A61B 17/80* (2006.01)
(52) U.S. Cl. ...................................................... 606/280
(58) Field of Classification Search .................. 606/280, 606/281, 283–285, 298
See application file for complete search history.

(56) References Cited

U.S. PATENT DOCUMENTS

| | | | |
|---|---|---|---|
| 2,791,868 A * | 5/1957 | Viken | 446/107 |
| 4,503,848 A * | 3/1985 | Caspar et al. | 606/280 |
| 4,966,599 A * | 10/1990 | Pollock | 606/915 |
| 5,372,598 A | 12/1994 | Luhr et al. | |
| 5,690,631 A * | 11/1997 | Duncan et al. | 606/281 |
| 5,814,048 A * | 9/1998 | Morgan | 606/283 |
| 6,093,188 A * | 7/2000 | Murray | 606/282 |
| 6,626,909 B2 * | 9/2003 | Chin | 606/276 |
| 6,635,087 B2 * | 10/2003 | Angelucci et al. | 623/17.11 |
| 6,711,432 B1 | 3/2004 | Krause et al. | |
| 6,772,026 B2 | 8/2004 | Bradbury et al. | |
| 7,052,499 B2 * | 5/2006 | Steger et al. | 606/291 |
| 7,344,538 B2 * | 3/2008 | Myerson et al. | 606/280 |
| 7,507,253 B2 * | 3/2009 | Nordquist | 623/16.11 |
| 7,909,860 B2 * | 3/2011 | Rathbun et al. | 606/290 |
| 7,963,980 B1 * | 6/2011 | Freeman et al. | 606/286 |
| 2005/0065521 A1 * | 3/2005 | Steger et al. | 606/69 |
| 2005/0283152 A1 * | 12/2005 | Lindemann et al. | 606/61 |
| 2006/0200145 A1 * | 9/2006 | Kay et al. | 606/69 |
| 2006/0235396 A1 * | 10/2006 | Sanders et al. | 606/69 |
| 2006/0235397 A1 * | 10/2006 | Sanders et al. | 606/69 |
| 2007/0073297 A1 * | 3/2007 | Reynolds | 606/69 |

\* cited by examiner

*Primary Examiner* — Kevin T Truong
*Assistant Examiner* — David Bates

(57) ABSTRACT

An implant for osteosynthesis used in the stabilization of fractured bone of the mandible. The plate consists of apertures through which the plate is secured to bone using surgical screws. The apertures are connected by (a) two lateral bar sections running approximately parallel to the long axis of the mandible and (b) two cross bar sections intersecting each other near the centroid of the plate and at acute angles to the lateral bar sections. The plate design can be modified to accommodate patient anatomy depending on the type of bone it is designed to stabilize. Design and size parameters of the fixation plate can be customized to each individual patient using a customization software application to determine the least invasive fixation plate that will provide adequate functioning in stabilizing the bone fracture to a degree that will allow safe bone healing. The invention includes a method of design of osteosynthesis plates using shape optimization for different types and locations of fractures.

14 Claims, 8 Drawing Sheets

OSTEOSYNTHESIS PLATE, METHOD OF CUSTOMIZING SAME, AND METHOD FOR INSTALLING SAME

CROSS REFERENCE TO RELATED APPLICATIONS

Provisional Application 60/790,488; filed Apr. 10, 2006; Applicant: Lovald; Title: Cranio maxillofacial implant device customization software.

Provisional Application 60/850,207; filed Oct. 10, 2006; Applicant: Lovald; Title: Osteosynthesis plate, method for customizing same, and method for installing same to stabilize bone fractures.

BACKGROUND OF THE INVENTION

1. Technical Field of Invention

The present invention pertains to a plate for fixation of broken bones. The osteosynthesis plate was designed to provide maximal stability over a bone fracture with a minimum of material and intrusion to the patient. The size of the shape of the fixation plate can be customized for each patient using a software application.

2. Description of Prior Art

U.S. Pat. No. 4,503,848 to Caspar, et al, issued Mar. 12, 1985 for an osteosynthesis plate shows a way to make possible the effective immobilization of pieces of bone with an osteosynthesis plate by making the longitudinal edges of the osteosynthesis plate diverge in the manner of a trapezoid, that the osteosynthesis plate be provided with two adjacent rows of slots for its screws, and that the orientations of the longitudinal axes of the slots in both rows diverge in the same directions as the diverging longitudinal edges of the osteosynthesis plate itself. The problem with this approach is that while this plate is a solid and stable structure adapted to fit the contours of many long bones, as a stabilizing structure it is over engineered as much of its solid material is not required to stabilize many common bone fractures throughout the body. A general rule of orthopedics is to find an implant that will perform adequately with a minimal volume and intrusion. In the case of osteosynthesis bone plates, stability of the fracture line is the primary concern of the implant as many complications stem from instability of the fracture region. These complications include infection, nonunion, and malunion of the fracture. While maximal stability of the fracture can be achieved through increasing the size and strength of the plate, there is both a limited number of materials capable of safe permanent implantation within the body and a limit to the size and shape of plates as increasing the volume of the plate can eventually cause complications due to the intrusive nature of the implant. Plate palpability, thermal sensitivity and stress shielding of bone are some complications incurred with plates of larger strength and volume. Furthermore, excessively large and stiff bone plates are cumbersome during surgery and can add significant time and cost to the procedure.

U.S. Pat. No. 5,372,598 to Luhr, et al, issued Dec. 13, 1994 describes the invention of a small bone plate suitable for use, for example, on the cranial skeleton, on the facial skeleton and on micro fragments of other skeleton sections. The bone plate is formed from webs joining screw hole boundaries in a particular fashion; and the plate can be bent in its plane, without deformation of the screw hole boundaries. The problem with this design is that it is a structure comprised solely of lateral bars that provide stability only in directions of compression and tension (pulling apart) within the fracture. An osteosynthesis plate for fractures should maximize stability by preventing relative movement of fractured bone pieces. Three major relative movements are seen in fractures of the mandible: separation or pulling apart of the fracture pieces in a direction normal to the plane of the fracture, lateral movement or shearing along the fracture plane in a direction approximately normal to the occlusal plane, and torsion of the fracture plane along the length of the mandible. The object of maximal osteosynthesis stabilization and minimal plate volume is only achieved through an optimal structure that combats all directions and moments of relative fracture movement.

U.S. Pat. No. 4,966,599 to Pollock, et al, issued Oct. 30, 1990 describes precontoured plating, screws, instruments and methods for osteosynthesis. Plates according to the present invention take advantage of the fact that human adult craniofacial structure and shape is highly similar among the population. The plates are thus preformed, pretempered, precontoured, and preconfigured during manufacture to fit a large proportion of the human adult population. The plates consequently require less time during surgery to twist and bend to conform to the skeletal structure and their crystalline and other structural characteristics need not be adversely affected by extensive bending, twisting and shaping in the operating room. The plates may be packaged and presented for use on forms which simulate portions of the skull so that their intended craniofacial location is easily recognized by members of the surgical team. In the case of the osteosynthesis plate used to fixate the mandibular ridge, the plate is contoured inappropriately. The part of the plate contacting the mandibular ramus should be situated further near to the anterior face of the ramus (which may require grinding the surface of the ridge), while the part of the plate contacting the mandibular body should be angled as much as possible so the screws remain nearer to the alveolar border of the mandible. The ideal form of the osteosynthesis plate is nearer to a mirror image of the plate described in Pollock.

U.S. Pat. No. 6,711,432 to Krause, et al, issued Mar. 23, 2004 describes the devices and methods for implementing computer aided surgical procedures and more specifically devices and methods for implementing a computer-aided orthopedic surgery utilizing intra-operative feedback. A three-dimensional model of an area of a patient upon which a surgical procedure is to be performed is modeled using software techniques. The software model is used to generate a surgical plan, including placement of multifunctional markers, for performing the surgical procedure. After the markers are placed on the patient, an updated image of the patient is taken and used to calculate a final surgical plan for performing the remainder of the surgical procedure. The three-dimensional modeling, surgical planning, and surgery may all take place remote from each other. The various entities may communicate via an electronic communications network such as the Internet. The problem with this method is that the software does not output any information as to the appropriate implant to use for the surgery nor does it output any information pertaining to the design parameters of an implant that would provide the best functioning for each patient. In the case of osteosynthesis, software of this nature should provide information describing design characteristics for an implant that will provide an environment for adequate fracture healing in each patient.

U.S. Pat. No. 6,772,026 to Bradbury, et al, issued Aug. 3, 2004 describes the rapid design and manufacture of biomedical devices such as implants, oral dosage pills and implantable pharmaceuticals employs electronic data and modeling transmissions via a computer network. Patient information and patient-specific radiological data is captured and transmitted via a computer network to a design and/or manufacturing site. A multi-dimensional digital model is created based on the radiological data and patient information. Communications interchanges between a clinical/diagnostic site and a design/manufacturing site permit modification of the digital model until approved. The approved digital model is converted into machine instructions to construct the biomedical device. Alternatively, the digital model is employed in a best fit selection of a biomedical device from a pre-existing set of biomedical devices or machine-instructions. Transmittal of data over computer networks is further directed to the use of a Website to perform various client-interaction and follow-up tasks. The problem with this method is that the design and customization process does not include an analysis that can optimize the design parameters of the biomedical implant based on analysis output measures that indicate the safety, adequacy, and intrusiveness of the implant. Sufficient stability of a bone fracture is required for adequate fracture healing. Instability or excessive movement in the presence of a foreign body can lead to infection and the subsequent nonunion of a fracture. An outcome of this type can require a second surgery to remove the hardware and provide more sufficient fixation. Furthermore, excessive stress imposed upon the osteosynthesis plate can lead to a failure of the plate, also requiring a second surgery. Adverse outcomes such as these can be avoided in employing a method using analysis of a model that includes patient specific data to determine the appropriate design parameters of an osteosynthesis plate that will lead to safe and adequate healing of a fracture.

SUMMARY OF THE INVENTION

The object of this invention is to create a plate of an optimal structure for osteosynthesis in that the implant provides maximal stability across the bone fracture while remaining minimally intrusive upon the patient. The design of the implant is done through shape optimization using a finite element or other mathematical solver. Size and shape parameters of each osteosynthesis plate can be customized to ensure adequate functionality and minimal invasiveness to each patient.

The task is accomplished according to the invention with an osteosynthesis plate with at least four screw holes arranged approximately in a box shape with bar sections: connecting the two superior screw holes of the plate to one another, and the two inferior screw holes of the plate to one another, approximately in a direction of the length of the mandible, preventing relative movement in the direction normal to the plane of the fracture; connecting each superior screw hole with its diagonal inferior screw hole resulting in an intersection of said bar sections near the centroid of the plate, preventing relative shearing motion along the fracture plane in a direction normal to the occlusal plane; and of a sufficient plate thickness to prevent torsion of the fracture plane along the length of the mandible. Any of the bar sections can be slightly arched to add further support to the structure. The base design has size parameters that can be either customized for each patient or selected before or during surgery from pre manufactured groups according to analysis based on input patient data. The basic shape described can be expanded upon or modified to accommodate patient anatomy.

It is the task of this invention to further develop a general design for an osteosynthesis plate of the known type that can maximize stability of any certain fracture type with a minimal amount of material while the region of the fracture undergoes naturally occurring loads. A basic plate design structure can be determined using shape optimization within a numerical method solver, for example, by using the finite element method. This act requires data input pertaining to the general anatomy and morbidity where the osteosynthesis plate is to be applied as well as the normal functioning loads or boundary conditions that are expected to be imposed on the region of interest. Given general geometrical and load data, along with biologic material properties of the region, a general optimized shape for an osteosynthesis plate can be determined for the specific application.

For patient customization, the ideal size parameters of a previously designed osteosynthesis plate for each patient can be determined through stress or strain analysis given a data input for each patient. Given patient input data including, for example, fracture location and bone quality, either a customized plate design or category of plate design and size can be determined for the patient. The determination can be based upon geometrical and spatial data from a geometrical model as well as stress and strain data from, for example, a finite element analysis based on the input patient data. The fracture plate can be either customized or selected from a variety of fracture plate types based upon the output of the aforementioned analyses. This will in turn provide the surgeon with an implant that delivers adequate functioning with minimal intrusion upon the patient.

BRIEF DESCRIPTION OF THE DRAWING FIGURES

DETAILED DESCRIPTION OF THE INVENTION

The present invention describes an implant for osteosynthesis, a method for installing same, a method for designing same, and a method for customizing same. The present invention may be specifically appropriate for designing, customizing, and installing plates for cranio maxillofacial surgery, though the invention is applicable to other types of surgery. References to fixation of fractures of the mandible, midface, and upper face are exemplary only.

Figure 1:
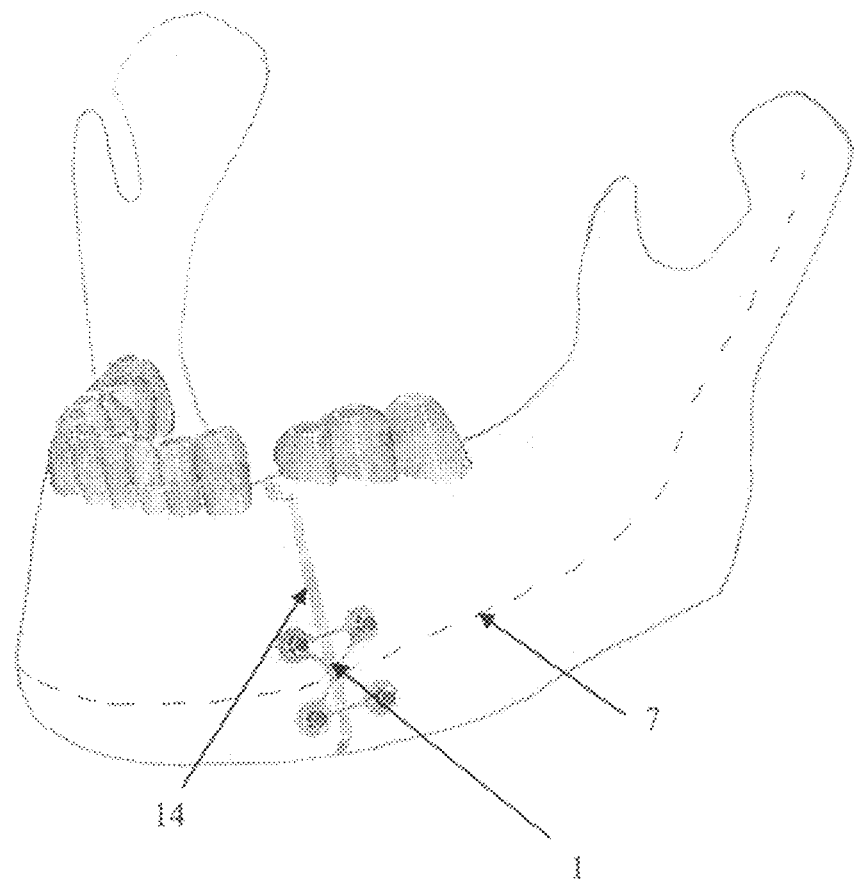
FIG. 1 is a view of an embodiment of the osteosynthesis plate in accordance with the present invention appropriately securing one of many fractures of which it is capable.

FIG. 1 shows a fracture 14 of the mandible fixated with an osteosynthesis plate 1. Mandibular fractures 14 can be located in different regions and can vary significantly in their severity. Rigid fixation of a fracture can be achieved by removing tissue to expose a bone fracture, bridging the fracture with an osteosynthesis plate, and securing the fixation plate to the patient anatomy by means of screws, pins, or tines. The purpose of rigid fixation of fractures is to provide adequate stability of the fracture so that a patient can assume a quick return to normal functioning. In order to avoid complications such as infection and nonunion of the fracture, an osteosynthesis plate should provide significant stability in the environment of the fracture as the patient returns to normal biting and mastication habits post surgery. Increasing the general size of the implant can increase the stability of the fracture region, but this act is inefficient if the fracture plate is not of an optimal structure as it can also lead to complications from stress shielding, sensory deficit, and patient palpability. The osteosynthesis plate should then be designed to provide maximal stability over a fracture when subjected to normal patient loading while also avoiding an unnecessarily large osteosynthesis plate. The optimal structure of an osteosynthesis plate depends entirely on the region of and the morbidity of the fracture, while the osteosynthesis plate size parameters depend upon, for example, patient specific variables such as the magnitude of naturally occurring loads and the bone quality of the patient.

An osteosynthesis plate for fractures should maximize stability by preventing relative movement of fractured bone pieces. Three major relative movements are seen in fractures of the mandible: separation (pulling apart) or compression of the fracture pieces in a direction normal to the plane of the fracture, lateral movement or shearing along the fracture plane in a direction normal to the occlusal plane, and torsion of the fracture plane along the length of the mandible. The object of maximal osteosynthesis stabilization and minimal plate volume is only achieved through an optimal structure that combats all directions and moments of relative fracture movement.

Figure 2:
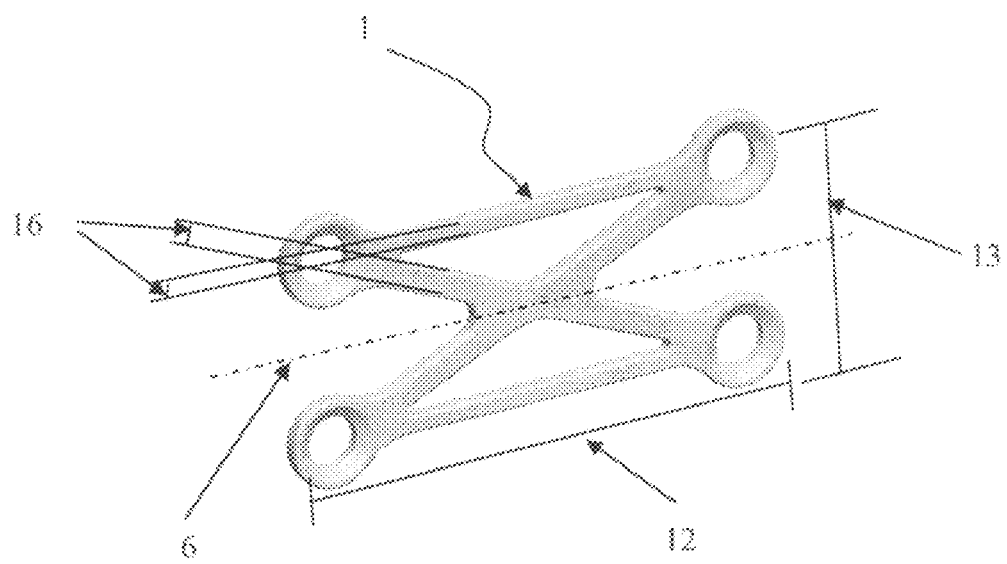
FIG. 2 is an isometric view of a solid model of an embodiment of the osteosynthesis plate according to the invention.
Figure 5:
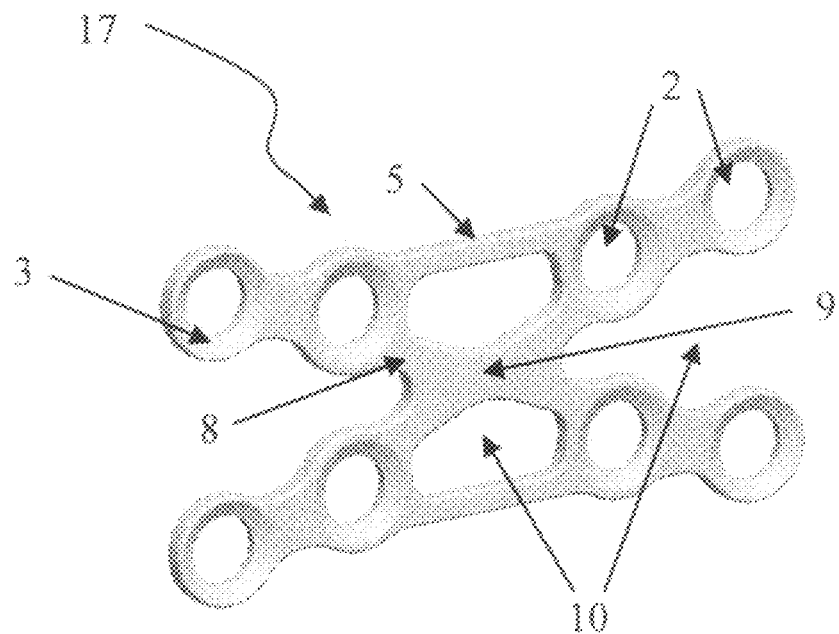
FIG. 5 is a plan view alternate embodiment of the present invention.
Figure 6:
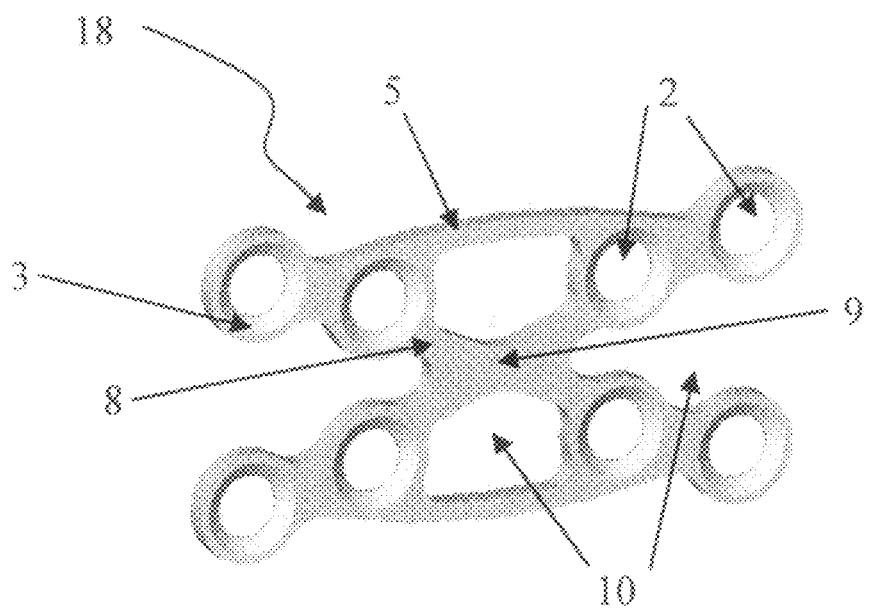
FIG. 6 is a plan view alternate embodiment of the present invention.

The best modes of the osteosynthesis plate of the present invention can be seen in FIGS. 5 and 6. Alternate embodiments can be seen in FIGS. 2, 3, 7, 9, and 10 further described herein. In FIG. 2, the osteosynthesis plate 1 represented in the illustrations has a rectangular/box shaped contour, the corners of which are holes 2 with countersinks 3 capable of accepting screws or screw type fasteners that secure the lower surface 4 of the plate to the surface of the bone. The countersinks 3 can be located on both sides of the fixation plate. Ideally at least two of these holes 2 will reside on each side of the fracture 14. The holes 2 may or may not be identically sized and may or may not lie aligned to one another in longitudinal rows.

In the best mode of the present invention, the screw holes 2 are connected by four bars. Two bars 5 connect the top/most superior holes 2 and the bottom/most inferior holes 2 as the longitudinal axis 6 of the plate is aligned approximately with the long axis of the bone to which it is secured 7. The purpose of the bars 5 aligned approximately parallel to the longitudinal axis 6 of the bone is to prevent motion in a direction approximately normal to the plane of the fracture 14. This is motion that leads to a separation or compression of the bone pieces secured by the osteosynthesis plate 1.

The screw holes are further connected by bars 8 crossing diagonally across the plate and intersecting near the centroid 9 of the osteosynthesis plate 1. The purpose of the bars 8 intersecting near the plate centroid 9 is to prevent shearing motion approximately along the plane of the fracture 14. The plate consists of at least 5% open area 10.

Figure 3:
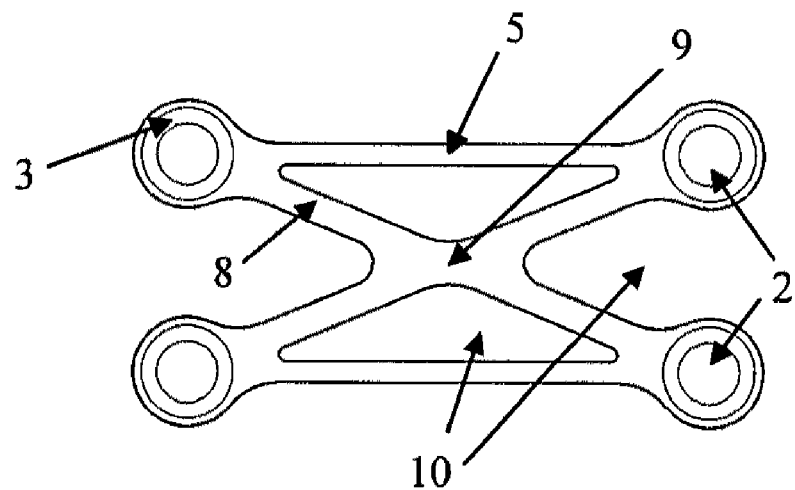
FIG. 3 is a front view of an embodiment of the osteosynthesis plate according to the invention.
Figure 4:
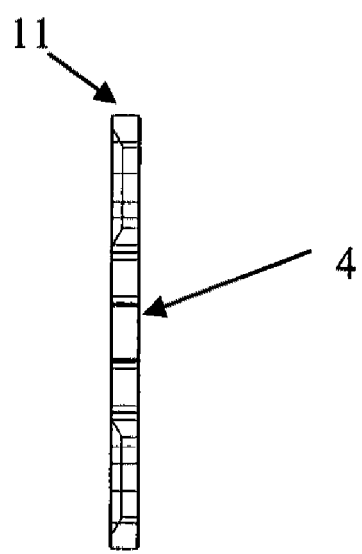
FIG. 4 is a side view of an embodiment of the osteosynthesis plate according to the invention.

FIG. 4 shows a side view of the osteosynthesis plate. The lower surface 4 may be planar or concave. The osteosynthesis plate 1 can be of any thickness 11 from 0.1 mm to 5 mm and can be formed anatomically to the contours of the bone to which it is secured. The thickness of the plate should be sufficient to resist torsion and out of plane bending of the fracture region when undergoing the naturally occurring loads of patients. FIG. 2 shows the overall dimensions of the osteosynthesis plate, while FIG. 3 shows some key design characteristics of the osteosynthesis plate. The length of the plate 12 along its longitudinal axis 6 can be of dimensions from 2 mm to 300 mm. The height of the plate 13 can be of dimensions from 2 mm to 300 mm. The lateral 5 and intersecting 8 material sections acting to connect the apertures 2 have a width 16 of 0.1 mm to 5 mm. The widths of each of these sections are independent from one another.

FIG. 1 shows appropriate placement of the osteosynthesis plate 1 to secure a fracture 14 of the mandible. The lateral bars 5 of the osteosynthesis plate 1 are aligned roughly with the long axis of the mandible 7. The lateral bars 5 resist a separation of the bone pieces in a direction normal to the plane of the fracture 14. The diagonal bars 8 intersect across the fracture providing resistance to shearing motion across the fracture 14. The thickness 11 of the osteosynthesis plate 1 is sufficient to resist torsion along the mandible fracture 14.

The plate can be fabricated of a bio-compatible metal or metallic alloy selected from the group consisting of titanium, titanium alloys, cobalt-chrome alloys, stainless steel, and any bio resorbable material. The plate can be made of any nano structured components of this included list of chemical make ups. These materials have all been deemed appropriate for implantation within the human body.

Alternate best modes 17,18 of the present invention can be seen in FIGS. 5 and 6, wherein the osteosynthesis plate 1 has four additional reinforced holes 2. The additional holes 2 give the surgeon more options to secure the plate to the patient bone during surgery. The centroid 9 is also larger and stronger while maintaining at least 5% open area 10.

An alternate best mode 18 of the present invention can be seen in FIG. 6, wherein the osteosynthesis plate 1 has four additional reinforced holes 2, while the lateral bars 5 are arched outward to give the plate 1 more support during in-plane bending.

Figure 7:
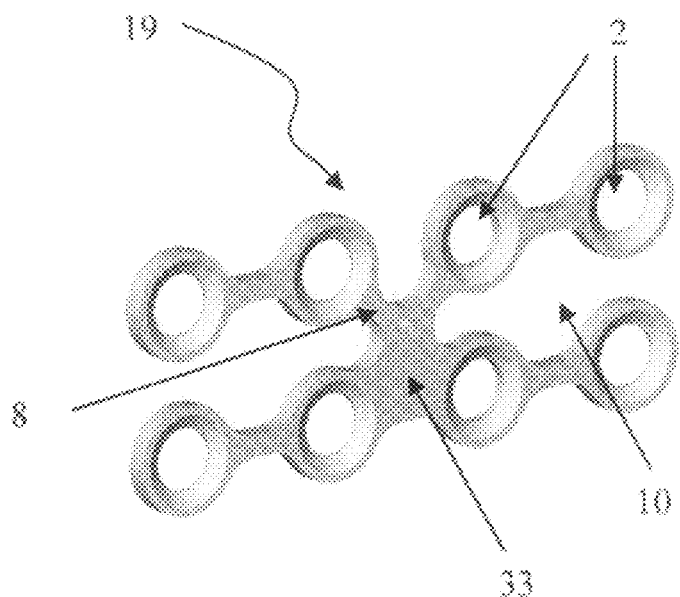
FIG. 7 is a plan view alternate embodiment of the present invention.
Figure 8:
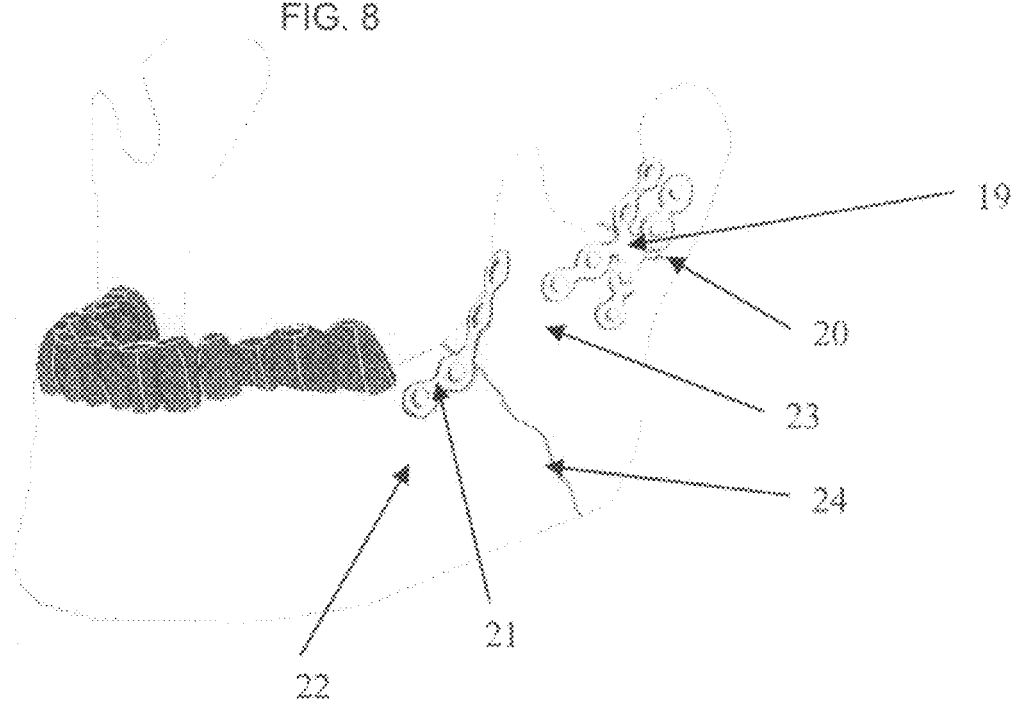
FIG. 8 is a diagram of the human mandible with fractures in the angle and subcondylar region secured with alternate embodiments of the present invention.

An alternate mode 19 of the present invention can be seen in FIG. 7, wherein the osteosynthesis plate 1 has been modified to accommodate patient anatomy. The superior lateral bar 5 has been removed to give more flexibility to the placement of the superior screw holes 2, while the inferior open space 10 of the plate has been converted to a solid section 33 to reinforce the plate. An example for appropriate use of this alternate embodiment 19 to fixate a fracture in the mandibular subcondylar region 20 is shown in FIG. 8. Depending on the anatomy to be fixated, the plate can be rotated to switch the placement of the stated superior and inferior sections.

Figure 9:
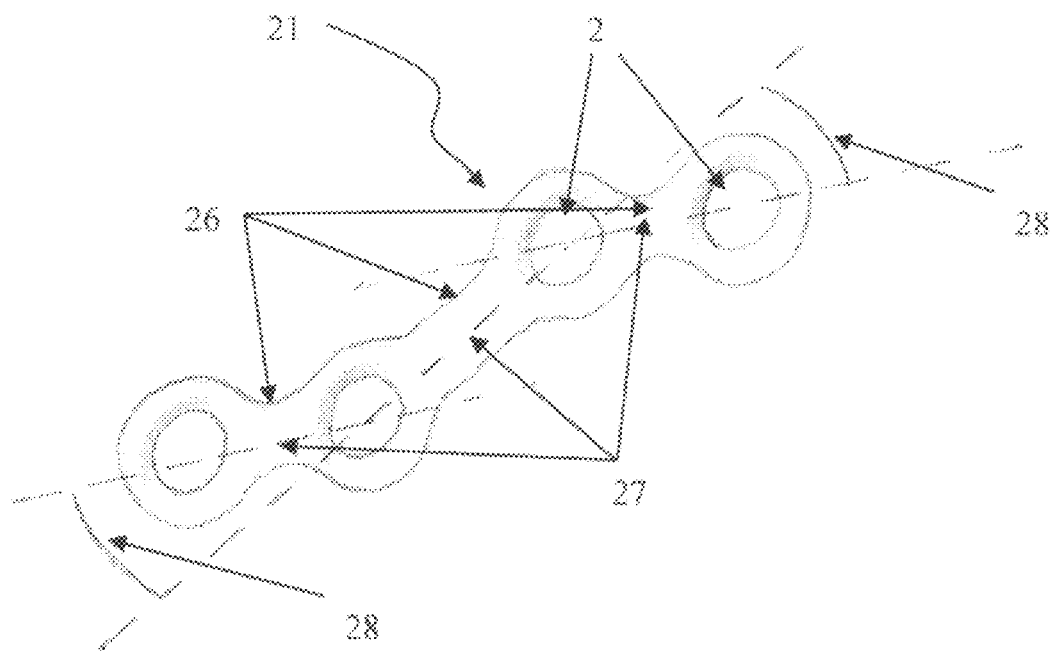
FIG. 9 is a plan view alternate embodiment of the present invention, designed specifically for fractures of the mandibular angle region.

An alternate mode 21 of the present invention can be seen in FIGS. 8 and 9, wherein the osteosynthesis plate 1 has been modified to accommodate patient anatomy specifically for placement near the region of intersection of the alveolar border of the mandibular body 22 and the anterior border of the mandibular ramus 23. FIG. 8 shows an example of appropriate placement of this osteosynthesis plate to secure a mandibular angle fracture 24. Fixation of angle fractures in this area is preferred as the method will often require no extra-oral incisions to place the plate. The difficulty though in plate fixation in this area is due to the bending and twisting of the plate to meet the contours of the patient anatomy. The alternate mode of the present invention 21 shown in FIGS. 8 and 9 accommodates the common patient anatomy of this region, requiring less work to fit the plate during surgery. The alternate mode 21 of the osteosynthesis plate 1 has apertures 2 capable of accepting screws that can be inserted to secure the osteosynthesis plate 21 to bone or pieces of bone. The apertures are connected by at least three material sections 26 whose longitudinal axes 27 are angled to one another. The angles 28 between the longitudinal axes 27 are independent of one another and can be within 5 degree and 80 degrees. The osteosynthesis plate 21 can be subjected to further bending or twisting of the basic plate shape in any direction. This can be done manually or with the aid of a tool or set of tools. The thickness of the plate should be sufficient to resist torsion and out of plane bending of the fracture region when undergoing the naturally occurring loads of patients.

Figure 10:
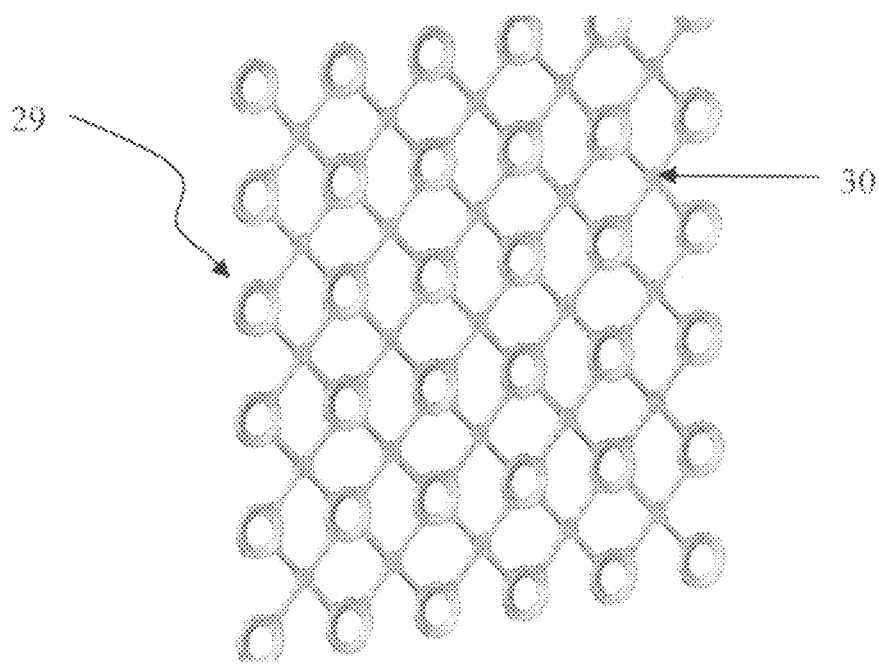
FIG. 10 is a plan view alternate embodiment of the present invention.
Figure 11:
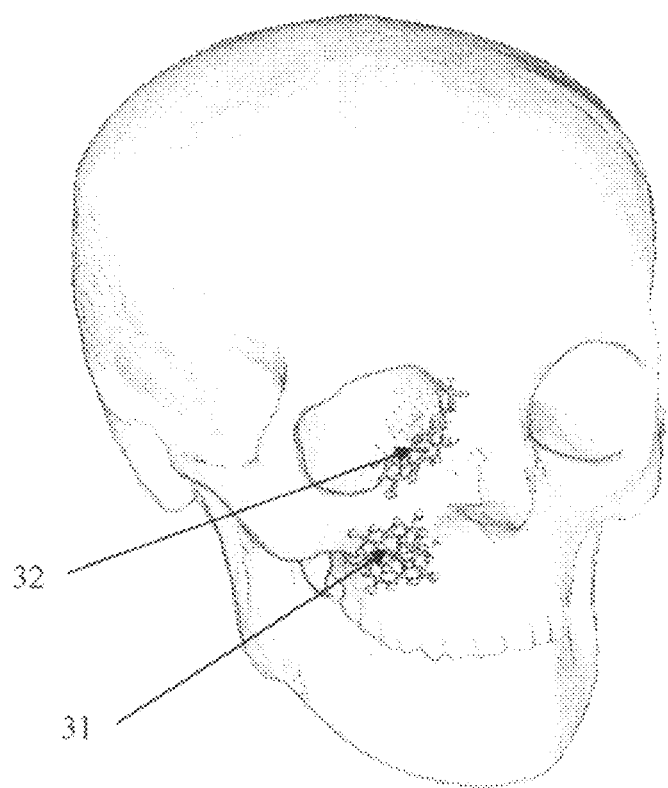
FIG. 11 is a diagram of the human skull showing the mesh design of the present invention used to fixate fractures of the midface and upper face.

An alternate mode 29 of the present invention can be seen in FIG. 10, wherein the osteosynthesis plate 1 has been modified as elements of the basic design structure are multiplied into a larger structure to form a mesh. The mesh structure can be modified during surgery by the surgeon to fit and fixate any fractures of the midface, upperface, and skull including orbital fractures, zygomatic complex fractures, LeFort I-III fractures, nasal-orbito-ethmoid fractures, or frontal sinus fractures. For example, FIG. 11 shows how the mesh could be used to fixate bone fragments in the in a LeFort I fracture 31 and a fracture of the medial orbital wall 32. The surgeon may use a scissors or other cutting instrument to cut the mesh to the shape and form required by the patient anatomy. The mesh should be of a thickness that can provide adequate functioning in fixation of bone fragments but should not be too thick as to disallow the surgeon to modify its shape with reasonable effort. The intersecting bars 30 of the mesh create a structure that can provide fracture fixation and stability for either load bearing or non load bearing bone. The lateral bars 5 are omitted in this alternate embodiment as the repeated structure provides a substitute for the same function the lateral bars 5 provided in the other described embodiments.

Figure 12:
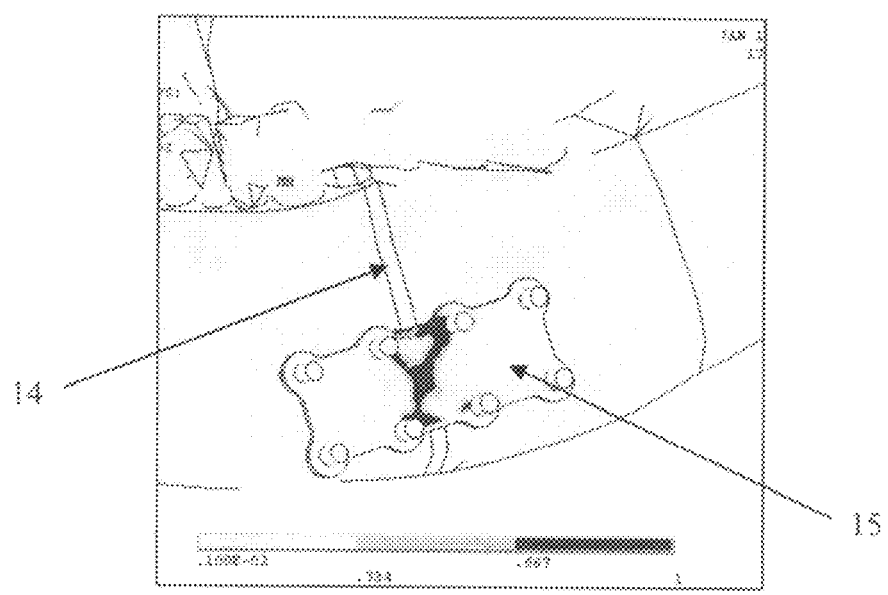
FIG. 12 is a diagram showing a fixation plate shape designed through shape optimization.

FIG. 12 shows an example of the design of osteosynthesis plates through shape optimization design. The plot is a standardized density plot with contours having a density scale of 0 to 1. Shape optimization of a bone plate can be achieved using, for example, a finite element model of an anatomical region with a certain degree of morbidity. The method of design using topological shape optimization starts with a formless solid plate 15 (without significant contours or shape) securing a specific location and type of fracture 14 with screws, pins, pegs, or tines. Considering the physical geometry, all material properties, and the loading or boundary conditions applied to the model, the program eliminates a specified percentage of the solid plate (X %) in a manner that maintains the stiffest, most stable environment possible in the fracture region when under physiological loading. The program finds an optimal structure for a specific fracture location. In the case of a fracture of the mandible the physical geometry could describe the three dimensional domain occupied by the cortical bone, cancellous bone, and dental segment that make up the larger mandible structure; the material properties could describe any of the linear or nonlinear material behavior of the different cortical and cancellous bone regions, dentin, enamel, and periodontal ligament as well as the fixation plate and screw material used to bridge the fracture; the boundary conditions could describe any biting or mastication forces being imposed upon the region. The shape optimization design procedure can be carried out on a general purpose computer.

Figure 13:
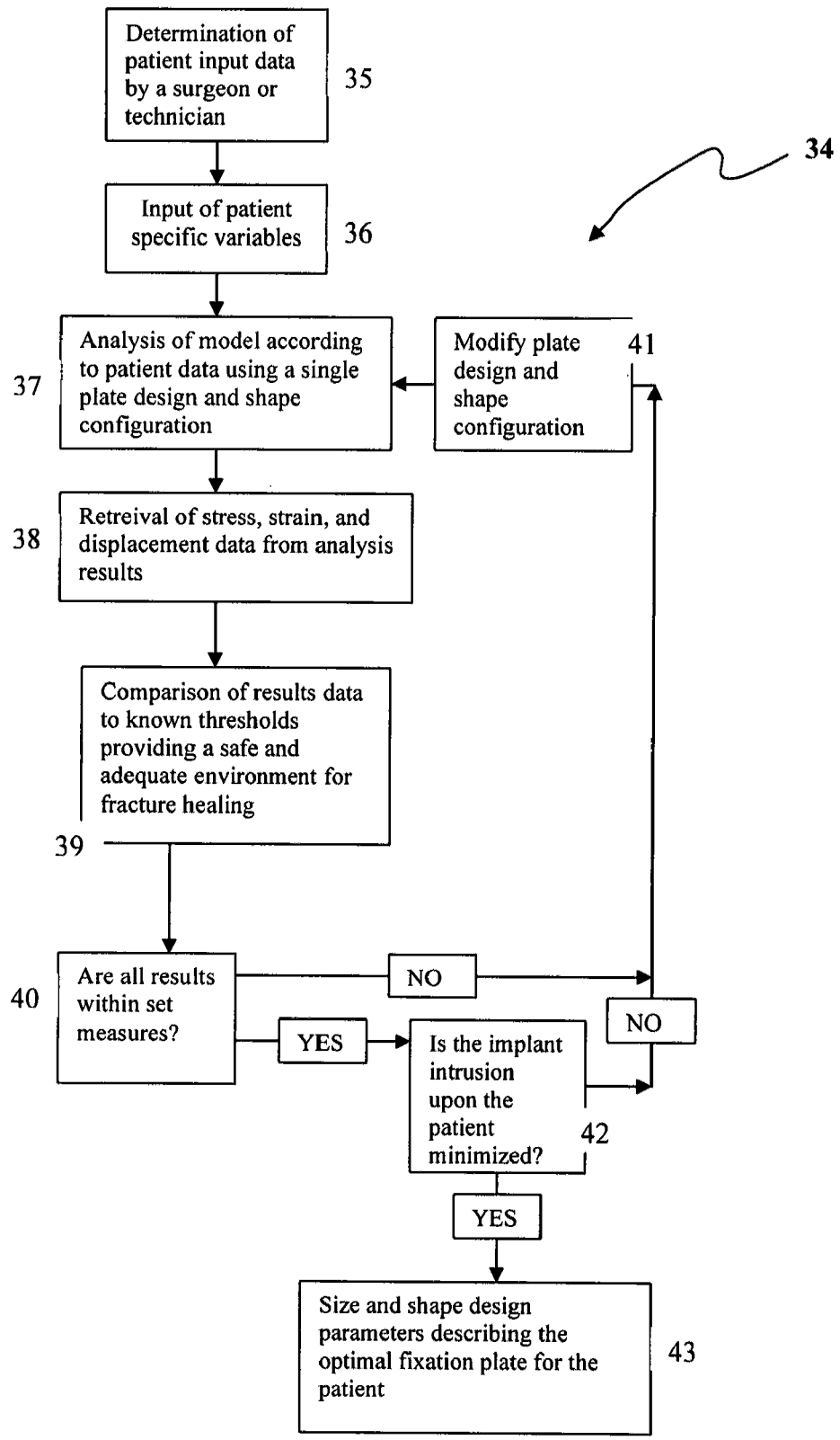
FIG. 13 is a flow chart detailing the osteosynthesis plate customization method.

An embodiment of the customization method 34 of the present invention is detailed as a flow chart in FIG. 13. Patient specific data possibly including but not limited to data pertaining to patient geometry, bone quality, fracture location, bite force magnitude, and fracture detail is gathered preoperatively by a surgeon or technician as indicated in Box 35. The data is input into a software application, indicated in Box 36, that will create a model to perform a numerical analysis and examine the performance of a specific size and shape of osteosynthesis plate. The data is can be input in, for example, numerical form or interactively with a graphical interface. The program selects an initial plate design and size to simulate the fixation of the patient fracture. An analysis is performed using the initial fixation plate as indicated in Box 37. Upon a clinically relevant physiological loading that is applied to the geometrical domain of the model, and given the material properties of all entities within the model, the simulation is capable of determining any of stress, strain, or displacement data in the osseous entities of the model, fracture, environment of the fracture, or any of the implant material, as indicated in Box 38. The Subproblem Approximation Method and the First Order Optimization Method are example algorithms capable of this type of procedure.

The application performs a multiple of analyses varying design and size parameters of the osteosynthesis plate. The software application will determine a set of design and size parameters of all possible fixation plate configurations that record output measures of any of stress, strain, and displacement that are within a threshold set in accordance with safe implant functioning and adequate fracture healing. This iterative process is indicated in Boxes 37 to 42. The software designates the best choice of osteosynthesis plate from the set of possible plates determined to be within these safety guidelines as indicated in Box 43. For example, the best choice could be the least intrusive osteosynthesis plate configuration that will perform adequately according to the output measures. The intrusion of the fixation plate could, for example, be based on the volume of the fixation plate. These steps can be processed by the data processing apparatus in FIG. 14.

The customization procedure may also calculate the optimal placement of the osteosynthesis plate and the screws used to secure the plate to the patients anatomy. Plate placement location can be varied, for example, from near to the superior occlusal border of the mandible to nearer to the inferior border of the mandible in the case of mandibular osteosynthesis. The analysis may include determining which screws, if all screw options are not to be utilized, provide the safest and most adequate environment for fracture healing.

The input parameters required to run the customization method can be determined by the surgeon or a technician from, for example, a collection of CT, MRI, or X-ray images. Patient data from these sources can be used to directly generate model requirements such as the geometry data describing the osseous and other biologic materials comprising the region of focus, material properties for the osseous and other biologic materials, data pertaining to morbidity of the region, and data pertinent to the types of loading to be imposed upon the model. Geometrical data can be transferred a program supporting the customization analysis using point cloud, curve, surface, or volumetric data from the original data set. Depending on the data type to be transferred, further work may be required. For example, if curves are transferred from the original data set, then likely surfaces and volumes will subsequently need to be created. Different material properties are designated to the geometric entities based on data from the original data set. For example, Hounsfield units can be measured on the original scans to determine the density and the mechanical behavior of the material. The mechanical material can be quantified, for example, with material constants such as the Modulus of Elasticity and Poisson's Ratio. The location and morbidity of the fracture can be determined from the original data and transferred into the customization model. Lastly, data pertaining to the expected loadings of the patient can be determined from the original patient data and incorporated into the customization model. For example, bone morphology along with patient data such as the sex, age, race, weight, and height of the patient can determine the appropriate type and magnitude of the physiological loading to be applied to the model.

Another example of a method to input geometrical patient data patient into the customization model is to first have the surgeon or technician take measurements from, for example, a collection of CT, MRI, or X-ray images and input data based on the measurements into a data table opening the software running the customization model. The measurement data could then modify or scale a pre-existing geometrical model. The location and morbidity of the fracture could be located either using a coordinate system or interactively with an interface that allowed the user to locate the fracture with, for example, a mouse connected to a general purpose computer. Other data pertaining to the morbidity of the fracture could be entered in numerically. Material data for the osseous and other biologic materials could be entered in numerically, as described before, after determination of their estimated values from all data available to the surgeon or other technician. Physiological loading could be entered in as described previously.

The output of the customization method could give the exact design parameters of an osteosynthesis plate that is to be fabricated and delivered to the surgery. This plate could either be fabricated on site with special equipment within the same facilities that house the surgery site, or the osteosynthesis plate could be fabricated at a remote location and delivered to the surgery site prior to its use. The fabrication of a perfectly customized osteosynthesis plate requires sufficient lead time for the diagnosis, data input, analysis, data output, plate fabrication, and delivery.

An alternate embodiment of the customization method would select the ideal osteosynthesis plate from a group of pre fabricated plates that are readily available to the surgeon. The surgeon would have access to a module that contains a number of categories of plate sizes and configurations. The software would select the appropriate plate category for each patient based on the customization analysis. While perfect customization is rarely possible with this embodiment, this alternative is both less expensive and requires less lead time. The necessary time for plate fabrication and delivery is eliminated and special fabrication machinery is not required proximal to the facilities housing the surgery.

The customization method can be carried out on a general purpose computer. Another option is to set up a data transfer system to a remote server. The input data can be sent from a general purpose computer via the internet or telephone to a remote location where a server will run the analyses and send the requisite results information back through the internet to the facility in which the surgery is to be housed.

Figure 14:
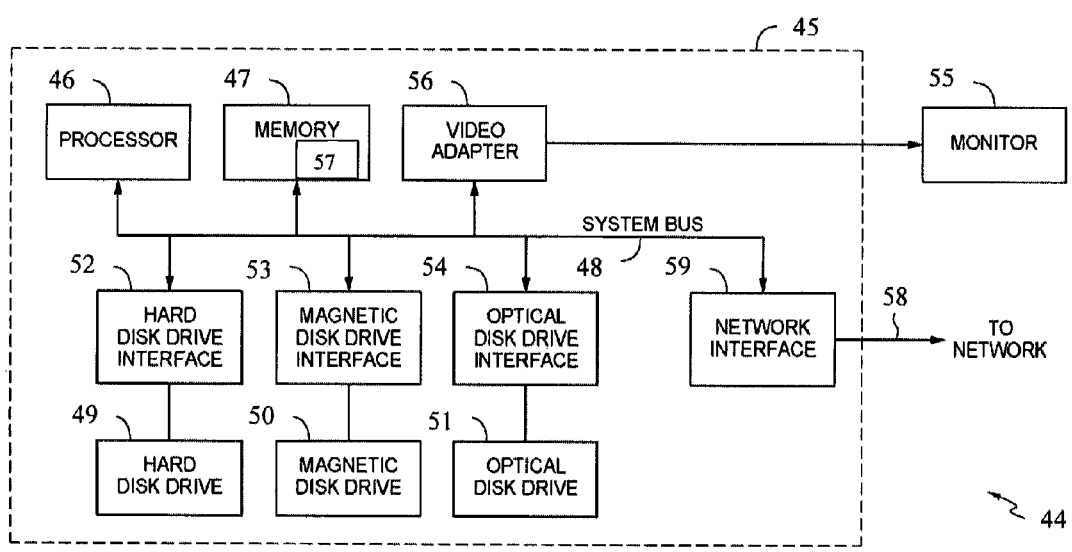
FIG. 14 illustrates a block diagram of a computer system, which can be adapted for use in implementing a preferred embodiment.

FIG. 14 illustrates a block diagram of a data-processing apparatus 44, which can be utilized to implement a preferred embodiment of the method for customizing size and shape parameters of an osteosynthesis plate. Data-processing apparatus 44 can be configured to include a general purpose computing device, such as a computer 45. The computer 45 includes a processing unit 46, a memory 47, and a system bus 48 that operatively couples the various system components to the processing unit 46. One or more processing units 46 operate as either a single central processing unit (CPU) or a parallel processing environment. It is noted that there are other types of computers that could act as the data-processing apparatus to implement an embodiment of the method for customizing size and shape parameters of an osteosynthesis plate. Examples of other data-processing apparatuses include, but are not limited to, a laptop computer or a Personal Digital Assistant (PDA).

The data-processing apparatus 44 further includes one or more data storage devices for storing and reading program and other data. Examples of such data storage devices include a hard disk drive 49 for reading from and writing to a hard disk (not shown), a magnetic disk drive 50 for reading from or writing to a removable magnetic disk (not shown), and an optical disc drive 51 for reading from or writing to a removable optical disc (not shown), such as a CD-ROM or other optical medium. A monitor 55 is connected to the system bus 48 through an adapter 56 or other interface. Additionally, the data-processing apparatus 44 can include other peripheral output devices such as speakers and printers.

The hard disk drive 49, magnetic disk drive 50, and optical disc drive 51 are connected to the system bus 48 by a hard disk drive interface 52, a magnetic disk drive interface 53, and an optical disc drive interface 54, respectively. These drives and their associated computer-readable media provide nonvolatile storage of computer-readable instructions, data structures, program modules, and other data for use by the data-processing apparatus 44. Note that such computer-readable instructions, data structures, program modules, and other data can be implemented as a module or group of modules, such as, for example, module 57.

The embodiments disclosed herein can be implemented in the context of a host operating system and one or more module(s) 57. In the computer programming arts, a software module can be typically implemented as a collection of routines and/or data structures that perform particular tasks or implement a particular abstract data type. In an embodiment of the computer implemented method to customize an osteosynthesis plate, a module to accept input of patient specific data, a module to execute a simulation, and a module to output useable data, in accordance with the procedure described in FIG. 13, are employed to determine the ideal osteosynthesis plate to fixate a specific patient's fracture.

Software modules generally comprise instruction media storable within a memory location of a data-processing apparatus and are typically composed of two parts. First, a software module may list the constants, data types, variable, routines and the like that can be accessed by other modules or routines. Second, a software module can be configured as an implementation, which can be private (i.e., accessible perhaps only to the module), and that contains the source code that actually implements the routines or subroutines upon which the module is based. The term module, as utilized herein can therefore refer to a single module or groups of software modules or implementations thereof. Such modules can be utilized separately or together to form a program product that can be implemented through signal-bearing media, including transmission media and recordable media.

Although the embodiments are described in the context of a fully functional data-processing apparatus such as data-processing apparatus 44, those skilled in the art will appreciate that the mechanisms of the present invention are capable of being distributed as a program product in a variety of forms, and that the present invention applies equally regardless of the particular type of signal-bearing media utilized to actually carry out the distribution. Examples of signal bearing media include, but are not limited to, recordable-type media such as floppy disks or CD ROMs and transmission-type media such as analogue or digital communications links.

Any type of computer-readable media that can store data that is accessible by a computer, such as magnetic cassettes, flash memory cards, digital versatile discs (DVDs), Bernoulli cartridges, random access memories (RAMs), and read only memories (ROMs) can be used in connection with the embodiments.

A number of program modules can be stored or encoded in a machine readable medium such as the hard disk drive 49, the, magnetic disk drive 50, the optical disc drive 51, ROM, RAM, etc or an electrical signal such as an electronic data stream received through a communications channel. These program modules can include an operating system, one or more application programs, other program modules, and program data.

The data-processing apparatus 44 can operate in a networked environment using logical connections to one or more remote computers (not shown). These logical connections are implemented using a communication device coupled to or integral with the data-processing apparatus 44. The data sequence to be analyzed can reside on a remote computer in the networked environment. The remote computer can be another computer, a server, a router, a network PC, a client, or a peer device or other common network node. FIG. 14 depicts the logical connection as a network connection 58 interfacing with the data-processing apparatus 44 through a network interface 59. Such networking environments are commonplace in office networks, enterprise-wide computer networks, intranets, and the Internet, which are all types of networks. It will be appreciated by those skilled in the art that the network connections shown are provided by way of example and that other means of and communications devices for establishing a communications link between the computers can be used.

We claim:

1. An osteosynthesis plate of a single solid piece in a box shape comprising:
    a plate having a structure with at least 25% of its footprint as open area;
    the plate having between 2 and 10 apertures for receiving screws;
    the plate having an upper surface for facing away from bone portions and a lower surface for contacting with the bone portions;
    the plate having screws that are adapted to be inserted in the apertures to secure the plate to the bone portions;
    the plate consisting of four truss members;
    the plate having a structure in which the apertures act as connecting points for the four truss members, the truss members including two parallel truss members which run parallel to one another in a direction along the length of the plate and two diagonal truss members which extend diagonally from four corners of the plate and cross diagonally and intersect at a solid continuous intersection without a screw hole near the centroid of the plate;
    wherein the diagonal truss members and parallel truss members meet at the four corners of the plate;
    wherein said intersection is the singular material connecting point on one symmetric line which runs parallel to said parallel truss members in the plane of the plate and said intersection and said parallel truss members are the only structures on a second symmetric line which is oriented normal to the first symmetric line in the plane of the plate;
    wherein each diagonal truss member extends continuously from one of the four corners of the plate to another of the four corners of the plate along a single, continuous, diagonal truss axis; and
    wherein the smallest angle formed between the diagonal truss members at the intersection is greater than or equal to forty-five degrees.

2. An osteosynthesis plate according to claim 1, wherein said osteosynthesis plate is fabricated of a bio-compatible metal or metallic alloy selected from the group consisting of titanium, titanium alloys, cobalt-chrome alloys and stainless steel, or of any bio resorbable material.

3. An osteosynthesis plate according to claim 1, wherein said screws have screw heads; and
    wherein said apertures are capable of receiving said screws and are beveled as a countersink so that each entire screw head is admitted into the thickness of the plate.

4. An osteosynthesis plate according to claim 1, wherein said truss members are arched in any direction.

5. An osteosynthesis plate according to claim 1, wherein the design is modified to accommodate patient anatomy.

6. An osteosynthesis plate according to claim 1, wherein elements of the basic design structure are multiplied into a larger structure to form a mesh.

7. An osteosynthesis plate according to claim 1, wherein each angle at the intersection is provided with a rounded configuration to reduce stress concentrations.

8. An osteosynthesis plate of a single solid piece in a box shape comprising:
    a plate having a structure with at least 25% of its footprint as open area;
    the plate having between 2 and 10 apertures for receiving screws;
    wherein the plate is adapted to be implanted to fixate a fracture of a patient's mandible in which there are mandibular bone portions, the plate having an upper surface for facing away from mandibular bone portions and a lower surface for contacting with the mandibular bone portions;
    the plate having screws that are inserted to secure the plate to the mandibular bone portions;
    the plate consisting of four truss members;
    the plate having a structure in which the apertures act as connecting points for the four truss members, the truss members including two parallel truss members which run parallel to one another in a direction along the length of the plate and two diagonal truss members which extend diagonally from four corners of the plate and cross diagonally and intersect at a solid continuous intersection near the centroid of the plate;
    wherein said intersection is the singular material connecting point on one symmetric line which runs parallel to said parallel truss members in the plane of the plate and said intersection and said parallel truss members are the only structures on a second symmetric line which is oriented normal to the first symmetric line in the plane of the plate;
    wherein the material at the intersection spans an area with a width to height ratio of approximately 1:1;
    wherein each diagonal truss member extends continuously from one of the four corners of the plate to another of the four corners of the plate along a single, continuous, diagonal truss axis;

wherein the smallest angle formed between the diagonal truss members at the intersection is greater than or equal to forty-five degrees;

wherein, when implanted, the two parallel truss members run approximately along the length of the mandible, preventing major relative motion between the mandibular bone portions in a direction normal to the plane of the fracture;

wherein, when implanted, the intersecting truss members prevent major relative motion between the mandibular bone portions in a direction parallel to the plane of the fracture; and wherein the thickness of the plate is sufficient to prevent major relative torsional motion between the mandibular bone portions around the long axis of the mandible.

9. An osteosynthesis plate according to claim 8, wherein said osteosynthesis plate is fabricated of a bio-compatible metal or metallic alloy selected from the group consisting of titanium, titanium alloys, cobalt-chrome alloys and stainless steel, or of any bio resorbable material.

10. An osteosynthesis plate according to claim 8, wherein said screws have screw heads; and wherein said apertures are capable of receiving said screws and are beveled as a countersink so that each entire screw head is admitted into the thickness of the plate.

11. An osteosynthesis plate according to claim 8, wherein said truss members are arched in any direction.

12. An osteosynthesis plate according to claim 8, wherein the design is modified to accommodate patient anatomy.

13. An osteosynthesis plate according to claim 8, wherein elements of the basic design structure are multiplied into a larger structure to form a mesh.

14. An osteosynthesis plate according to claim 8, wherein each angle at the intersection is provided with a rounded configuration to reduce stress concentrations.

* * * * *